United States Patent
Cholli et al.

(10) Patent No.: US 7,323,511 B2
(45) Date of Patent: Jan. 29, 2008

(54) POST-COUPLING SYNTHETIC APPROACH FOR POLYMERIC ANTIOXIDANTS

(75) Inventors: Ashok L. Cholli, Chelmsford, MA (US); Ashish Dhawan, Lowell, MA (US); Vijayendra Kumar, Lowell, MA (US)

(73) Assignee: University of Massachusetts Lowell, Lowell, MA (US)

( * ) Notice: Subject to any disclaimer, the term of this patent is extended or adjusted under 35 U.S.C. 154(b) by 313 days.

(21) Appl. No.: 11/040,193

(22) Filed: Jan. 21, 2005

(65) Prior Publication Data

US 2005/0238789 A1 Oct. 27, 2005

Related U.S. Application Data

(60) Provisional application No. 60/537,983, filed on Jan. 21, 2004.

(51) Int. Cl.
*C08F 8/00* (2006.01)
*A23L 3/3481* (2006.01)
*C10M 145/00* (2006.01)

(52) U.S. Cl. ........................... 524/611; 525/50
(58) Field of Classification Search ................ 524/611; 525/50
See application file for complete search history.

(56) References Cited

U.S. PATENT DOCUMENTS

| | | | |
|---|---|---|---|
| 3,294,836 A | 12/1966 | Peterson et al. | |
| 3,441,545 A | 4/1969 | Blatz et al. | |
| 3,459,704 A | 8/1969 | Peterson et al. | |
| 3,632,785 A | 1/1972 | Bornstein | |
| 3,645,970 A | 2/1972 | Kleiner | |
| 3,655,831 A | 4/1972 | Friedman | |
| 3,996,160 A | 12/1976 | Dale et al. | |
| 3,996,198 A | 12/1976 | Wang et al. | |
| 4,094,857 A | 6/1978 | Wolfe, Jr. | |
| 4,098,829 A | 7/1978 | Weinshenker et al. | |

(Continued)

FOREIGN PATENT DOCUMENTS

CS 111291 6/1964

(Continued)

OTHER PUBLICATIONS

Jialanella et al. [Synthesis of Poly(Vinyl Alcohol-Co-Vinyl Gallate) by the Chemical Modification of Poly(Vinyl Alcohol), Polymer Bulletin, 18(5):385-389 (1987)].*

(Continued)

*Primary Examiner*—Kelechi C. Egwim
(74) *Attorney, Agent, or Firm*—Hamilton, Brook, Smith & Reynolds, P.C.

(57) ABSTRACT

A method of preparing an antioxidant polymer includes forming or obtaining a first polymer having reactive pendant groups, where the first polymer does not include cyclic anhydride repeat units, and derivatizing the first polymer with an antioxidant. Another method of preparing an antioxidant polymer includes forming or obtaining a first polymer having reactive pendant groups and derivatizing the first polymer with an antioxidant, where the antioxidant is attached to the first polymer by an acetal, amide, amine, carbamate, carbonate, ester, ether or thioether linkage or by a carbon-carbon bond. The invention is also directed to polymers that are generally prepared by these methods, compositions that include such polymers and methods of using such polymers.

6 Claims, 1 Drawing Sheet

U.S. PATENT DOCUMENTS

| | | |
|---|---|---|
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,341,879 A | 7/1982 | Sugio et al. |
| 4,355,148 A | 10/1982 | Layer et al. |
| 4,377,666 A | 3/1983 | Farrar |
| 4,447,657 A | 5/1984 | Firth et al. |
| 4,465,871 A | 8/1984 | Firth et al. |
| 4,511,491 A | 4/1985 | Ishii et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,900,671 A | 2/1990 | Pokora et al. |
| 4,968,759 A | 11/1990 | Kikuchi et al. |
| 4,977,004 A | 12/1990 | Bettle, III et al. |
| 5,013,470 A | 5/1991 | Benfaremo |
| 5,017,727 A | 5/1991 | Olivier |
| 5,143,828 A | 9/1992 | Akkara et al. |
| 5,206,303 A | 4/1993 | Tse et al. |
| 5,207,939 A | 5/1993 | Farng et al. |
| 5,320,889 A | 6/1994 | Bettle, III |
| 5,449,715 A | 9/1995 | Plochocka et al. |
| 5,574,118 A | 11/1996 | Olivier |
| 5,834,544 A | 11/1998 | Lin et al. |
| 5,911,937 A | 6/1999 | Hekal |
| 5,994,498 A | 11/1999 | Tripathy et al. |
| 6,018,018 A | 1/2000 | Samuelson et al. |
| 6,150,491 A | 11/2000 | Akkara |
| 6,342,549 B1 | 1/2002 | Hirose et al. |
| 6,444,450 B2 | 9/2002 | Akkara et al. |
| 6,770,785 B1 | 8/2004 | Desai et al. |
| 6,828,364 B2 | 12/2004 | Gugumus |
| 7,223,432 B2 | 5/2007 | Cholli et al. |
| 2001/0041203 A1 | 11/2001 | Uno et al. |
| 2002/0128493 A1 | 9/2002 | Romanczyk, Jr. et al. |
| 2002/0183470 A1 | 12/2002 | Tripathy et al. |
| 2003/0030033 A1 | 2/2003 | Duyck et al. |
| 2003/0191242 A1 | 10/2003 | Zedda et al. |
| 2004/0164279 A1 | 8/2004 | Stevenson et al. |
| 2004/0186167 A1 | 9/2004 | Dou et al. |
| 2004/0214935 A1 | 10/2004 | Cholli et al. |
| 2006/0029706 A1 | 2/2006 | Cholli et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0189824 A1 | 8/2006 | Kumar et al. |
| 2006/0233741 A1 | 10/2006 | Kumar et al. |
| 2007/0106059 A1 | 5/2007 | Cholli et al. |
| 2007/0135539 A1 | 6/2007 | Ashok et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |

FOREIGN PATENT DOCUMENTS

| | | |
|---|---|---|
| DE | 197 47 644 A1 | 5/1999 |
| DE | 19843875 | 3/2000 |
| EP | 0 181 023 A1 | 5/1986 |
| EP | 0 289 077 A2 | 11/1988 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1067144 A1 * | 1/2001 |
| EP | 1468968 | 10/2004 |
| FR | 2 183 973 | 12/1973 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |
| JP | 59197447 | 11/1984 |
| JP | 60-199832 | 10/1985 |
| JP | 05 199858 | 8/1993 |
| JP | 06 247959 | 9/1994 |
| JP | 08027226 A | 1/1996 |
| JP | 09262069 | 10/1997 |
| JP | 9322784 A | 12/1997 |
| JP | 09328519 | 12/1997 |
| JP | 09328519 A * | 12/1997 |
| JP | 09328521 | 12/1997 |
| JP | 09328521 A * | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 01/18125 A1 | 3/2001 |
| WO | WO 01/48057 A1 | 7/2001 |
| WO | WO 02/079130 A1 | 10/2002 |
| WO | WO 03/087260 A1 | 10/2003 |
| WO | WO 03/102004 A1 | 12/2003 |
| WO | WO 2004/024070 A2 | 3/2004 |
| WO | WO 2004/050795 A2 | 6/2004 |
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WP 2006/018403 A1 | 2/2006 |
| WO | WO 2006/060801 A2 | 6/2006 |
| WO | WO 2006/104957 A2 | 10/2006 |

OTHER PUBLICATIONS

Singh et al. ["Biocatalytic Route to Ascorbic Acid-Modified Polymers for Free-Radical Scavenging," Adv. Mater., 15(15): 1291-1294 (2003)].*

Jialanella, G., et al., Synthesis of Poly(Vinyl Alcohol-Co-Vinyl Gallate) by the Chemical Modification of Poly(Vinyl Alcohol), *Polymer Bulletin*, 18(5):385-389 (1987).

Jayaprakasha, G.K., et al., *Food Chemistry*, 73: 285-290 (2001).

Singh, A., et al., "Biocatalytic Route to Ascorbic Acid-Modified Polymers for Free-Radical Scavenging," *Adv. Mater.*, 15(15): 1291-1294 (2003).

Kim, T.H., et al., "Melt Free-Radical Grafting of Hindered Phenol Antioxidant onto Polyethylene," *J. Appl. Polymer Science*, 77: 2968-2973 (2000).

Dordick, J.S., et al., "Polymerization of Phenols Catalyzed by Peroxidase in Nonaqueous Media," *Biotechnology and Bioengineering*, XXX:31-36 (1987).

Kazandjian, R.Z., et al., "Enzymatic Analyses in Organic Solvents," *Biotechnology and Bioengineering*, XXVIII:417-421 (1986).

Klibanov, A.M., et al., "Enzymatic Removal of Toxic Phenols and Anilines from Waste Waters," *J. of Applied Biochemistry*, 2(5):414-421 (1980).

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).

Ayyagari, M.S., et al., "Controlled Free-Radical Polymerization of Phenol Derivatives by Enzyme-Catalyzed Reactions in Organic Solvents," *Macromolecules*, 28(15):5192-5197 (1995).

Ryu, K., et al., "Peroxidase-Catalyzed Polymerization of Phenols," Biocatalysis in Agricultural Biotechnology, Chapter10:141-157 (1988).

Bruno, F.F., et al., "Enzymatic Template Synthesis of Polyphenol," Materials Research Society Symposium Proceedings vol. 600, Electroactive Polymers (EAP):255-259 (1999).

Akkara, J.A., et al., "Hematin-Catalyzed Polymerization of Phenol Compounds," Macromolecules, 33(7):2377-2382 (2000).

Dordick, J.S., "Enzymatic Catalysis in Monophasic Organic Dolvents," *Enzyme Microb. Technol.*, 11(4):194-211 (1989).

FS&T 821 "Food Lipids," [online], Oct. 2001 [retrieved on Oct. 29, 2002]. Retrieved from the Internet <URL: http://class.fst.ohio-state.edu/fst821/>.

FST 821 "Course Schedule," [online], [retrieved on Oct. 29, 2002]. Retrieved from the Internet <URL: http://class.fst.ohio-state.edu/fst821/>.

FS&T 821 "Antioxidant," [online], [retrieved on Oct. 29, 2002]. Retrieved from the Internet <URL: http://class.fst.ohio-state.edu/fst821/>.

Hidalgo, M.E., et al., "Antioxidant Activity of Depsides and Depsidones," Phytochemistry, 37(6):1585-1587 (1994).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

March, J., Advanced Organic Chemistry, McGraw Hill Book Company, New York, pp. 251-259 (1977).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Masada, H. and Oishi, Y., "A New Synthesis of aryl *t*-butyl Ethers," *Chem. Letters*, 57-58 (1978).

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Masada, H., et al., "A New Method for the Williamson Ether Synthesis Using *t*-alkyl Halides in Nonpolar Solvents," *The Chemical Society of Japan*, 2:164-166 (1995).

Masada, H. et al., "A New Heterogeneous Williamson Synthesis of Ethers Using *t*-alkyl Substrates," The *Chemical Society of Japan* 3:275-282 (1996).

Tsvetkov, O.N., et al., "Alkylation of Phenols with Higher Olefins. Part I," *Int. Chem. Eng.* 7(1):104-121 (1967).

Sartori G., et al., "Highly Selective Mono-*tert*-butylation of Aromatic Compounds," *Chem. Ind.*, (London), (22):762-763 (1985).

Koshchii, V.A., et al. "Alkylation of Phenol by Alcohols in the Presence of Alumium Phenolate," *Org. Chem.* 24(7):1358-1361 (1988).

Chandra, K.G. and Sharma, M.M., "Alkylation of Phenol with MTBE and Other tert-butylethers:Cation Exchange Resins as Catalysts," *Catal. Lett.* 19(4):309-317 (1993).

Sakthivel, A., et al., "Vapour Phase Tertiary Butylation of Phenol Over Sulfated Zirconia Catalyst," *Catal. Lett.*, 72(3-4):225-228 (2001).

Quaschning, V., et al., "Properties of Modified Zirconia Used as Friedel-Crafts-Acylation Catalysts," *J. Catal.* 177:164-174 (1998).

Badamali, S.K., et al., "Influence of Aluminium Sources on the Synthesis and Catalytic Activity of Mesoporous AIMCM-41 Molecular Sieves," *Catal. Today* 63:291-295 (2000).

Heidekum, A., et al., "Nafion/Silica Composite Material Reveals High Catalytic Potential in Acylation Reactions," *J. Catal.* 188:230-232 (1999).

Kamitori, Y., et al., "Silica Gel as an Effective Catalyst for the Alkylation of Phenols and Some Heterocylic Aromatic Compounds," *J. Org. Chem.* 49: 4161-4165 (1984).

Armengol, E., et al., "Acid Zeolites as Catalysts in Organic Reactions, *tert*-Butylation of Anthracene, Naphthalene and Thianthrene," *Appl. Catal. A* 149:411-423 (1997).

Lalancette, J.M., et al., "Metals Intercalated in Graphite. II. The Friedel-Crafts Reactions with $ALCL_3$-Graphite," *Can. J. Chem.* 52:589-591 (1974).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Devassy, B.M., et al., "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119 (2004).

XP-002419239, "Discover Our World of Effects for Polyolefins," *Ciba Speciality Chemicals*, (2003).

Pirozhenko, V.V., et al., "NMR Study of Topomerization of *N*-Aroyl-*p*-Benzoquinonemonoimines," *Russian J. of Organic Chem.*, 31(11):1514-1519 (1995).

Coppinger, G.B., et al., "Photo-Fries Rearrangement of Aromatic Esters. Role of Steric and Electronic Factors" *J. of Phy. Chem.*, 70(11):3479-3489 (1966).

Spano, R., et al., "Substituted Anilides of 3-Monoethyl Ester of 4 Hydroxyisophthalic Acid," *J. of Med. Chem.*, 15(5):552-553 (1972).

Mejias, L., et al., "New Polymers From Natural Phenols Using Horseradish or Soybean Peroxidase," *Macromol. Biosci.*, 2:24-32 (2002).

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Belyaev, A., et al., "Structure-Activity Relationship of Diaryl Phosphonate Esters as Potent Irreversible Dipeptidyl Peptidase IV Inhibitors," *J. Med. Chem.*, 42:1041-1052 (1999).

Blokhin, Y.I, et al., "Phosphorylation of Dihydric Phenols with Amides of Phosphorous Acid," *Russian Chem. Bulletin*, 45(9):2250-2251 (1996).

Pätoprstý, V., et al., "$^{13}C$ NMR Study of 3,9-Di(alkylpheonxy)-2,4,8,10-tetraoxa-3,9-diphosphaspiro[5.5]undecanes," *Magnetic Resonance in Chem*, 23(2):122-126 (1985).

Faber, K., "Biotransformations in Organic Chemistry," A Textbook, Fourth Completely Revised and Extended Edition, Springer-Verlag pp. 347-349 (1953).

\* cited by examiner

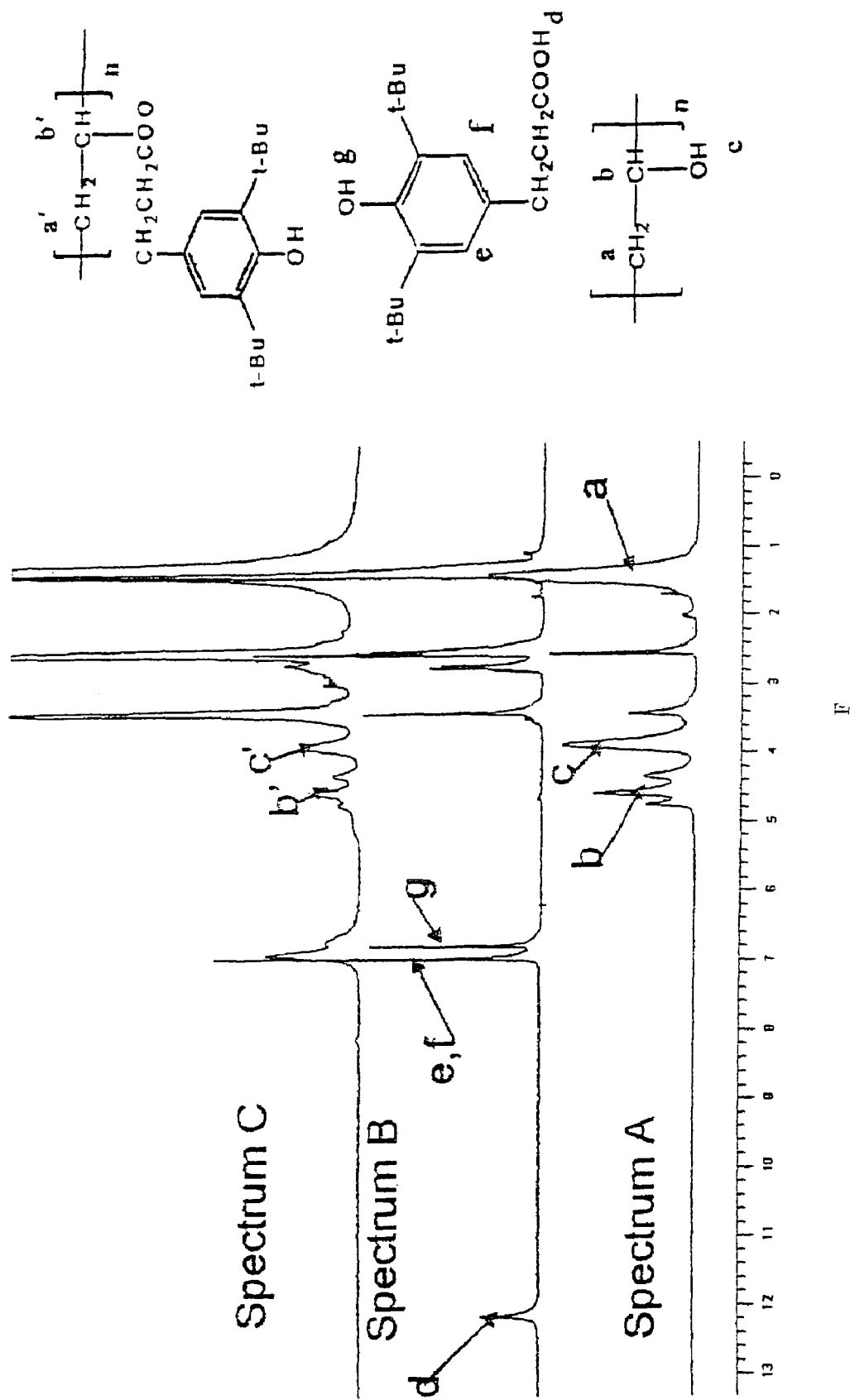

POST-COUPLING SYNTHETIC APPROACH FOR POLYMERIC ANTIOXIDANTS

RELATED APPLICATION

This application claims the benefit of U.S. Provisional Application No. 60/537,983, filed Jan. 21, 2004, the entire teachings of which are incorporated herein by reference.

GOVERNMENT SUPPORT

The invention was supported, in whole or in part, by a grant DMR-9986644 from the National Science Foundation. The Government has certain rights in the invention.

BACKGROUND OF THE INVENTION

Synthetic antioxidant preservatives are added to a wide variety of products during processing and storage. The types of products include foods, plastics and packaging materials. When an oxidizing event takes place in a product, the antioxidant molecules rapidly react to form antioxidant radicals. This reaction protects the product from damage resulting from the oxidizing event and consequently increases the shelf life of the product. Common synthetic antioxidant preservatives include butylated hydroxyanisole (BHA), butylated hydroxytoluene (BHT), tert-butylhydroquinone (TBHQ), di-tert-butylhydroquinone (DTBHQ), and propyl gallate. There are also naturally occurring antioxidants, which include sesamol, sesamin, vitamin A and beta-carotene, vitamin E and tocopherols and vitamin C.

The use of antioxidant preservatives can be particularly common in foods with significant unsaturated lipid content. These foods also contain quantities of unsaturated fatty acids. Unsaturation in fatty acids makes lipids susceptible to oxidation, which in turn leads to complex chemical changes in the lipids. These chemical changes eventually manifest themselves in the development of off-flavors (rancidity) in foods. The oxidation of unsaturated fatty acids can typically be mediated by free radicals, which can be caused by heat, light, ionizing radiation, trace metals and some proteins. The use of antioxidant preservatives in lipid-containing foods minimizes rancidity, retards the formation of toxic oxidation products, allows maintenance of nutritional quality and increases the shelf life. The mechanism by which the antioxidant preservatives are believed to act involves scavenging peroxyl radicals and preventing propagation of the oxidation process. The antioxidant activity of these compounds can be lost upon scavenging a free radical, so a food or other product can be no longer protected from oxidation once all the antioxidant preservative has reacted with a free radical. In other words, the degree of protection from oxidation can depend on the quantity of antioxidant preservative that is present.

Unfortunately, there are restrictions on the amount of synthetic antioxidant preservatives that can be added to a product, especially products intended for human or animal consumption. The U.S. Food and Drug Administration limits the amount of BHA and BHT in foods to 0.02% of total fat, because these compounds are suspected to be carcinogenic.

Consequently, there is a need for a new class of synthetic antioxidant preservatives that are less toxic to humans and animals. Also, it would be advantageous to develop an antioxidant preservative with increased potency and the ability to be readily processed with a variety of materials. Antioxidant preservatives with these improved properties would increase the shelf life and palatability of lipid-containing food items, as well as other products containing moieties (e.g., unsaturated carbon-carbon bonds) that can be damaged by free radicals.

SUMMARY OF THE INVENTION

A first aspect of the present invention includes a method of preparing an antioxidant polymer, which includes the steps of:

i) forming or obtaining a first polymer having reactive pendant groups, where the first polymer does not include cyclic anhydride repeat units; and ii) derivatizing the first polymer with an antioxidant.

In another aspect, the invention relates to a method of preparing an antioxidant polymer that includes:

i) forming or obtaining a first polymer having reactive pendant groups; and ii) derivatizing the first polymer with an antioxidant, wherein the antioxidant is attached to the first polymer by an acetal, amide, amine, carbamate, carbonate, ester, ether or thioether linkage or by a carbon-carbon bond.

A further aspect of the invention includes an antioxidant polymer produced by the process that involves derivatizing a homopolymer or a block, star, hyperbranched, random, gradient block, or alternate copolymer with one or more phenolic antioxidants. The phenolic antioxidants can be attached to the homopolymer or the block, star, hyperbranched, random, gradient block, or alternate copolymer by an acetal, amine, carbamate, carbonate, ester, ether or thioether linkage.

In one embodiment, the invention relates to a polymer having at least one repeat unit that is represented by a structure selected from the group consisting of Structural Formulas (I), (II), (III), (IV) and combinations thereof:

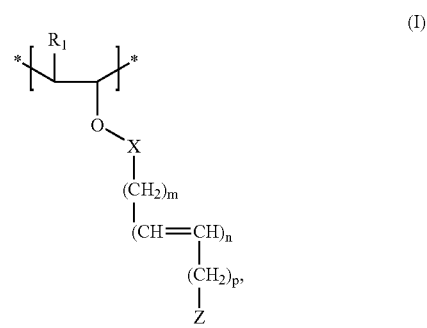

(I)

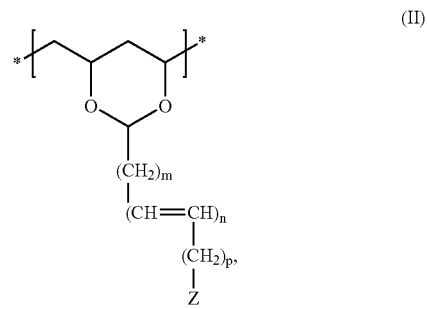

(II)

-continued

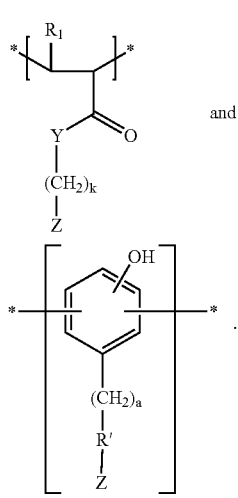

(III)

and (IV)

R' is a covalent bond, —O—, —C(O)O—, —C(O)N—, —C(O)—, —CH=CH—, —S— or —N—.

$R_1$ is —H or an alkyl group, or —(CH$_2$)$_k$—O—X-Z. Typically, $R_1$ is —H or alkyl.

Each X is independently a covalent bond, —C(O)—, —C(O)O— or —C(O)N—.

Y is —O—, —N— or —S—.

Each Z is an independently selected antioxidant.

a is an integer from 0 to 12.

Each k is independently an integer from 0 to 12.

m is an integer from 0 to 6.

n is 0 or 1.

p is an integer from 0 to 6.

Another aspect of the present invention relates to a method of inhibiting oxidation of a substance, which includes the step of contacting the substance with an antioxidant polymer produced by the process having the step of derivatizing a homopolymer or a block, star, hyperbranched, random, gradient block, or alternate copolymer with one or more phenolic antioxidants, where the phenolic antioxidants can be attached to the homopolymer or the block, star, hyperbranched, random, gradient block, or alternate copolymer by an acetal, amine, carbamate, carbonate, ester, ether or thioether linkage.

In another aspect, the invention includes a method of inhibiting oxidation of a substance, which includes the step of contacting the substance with a polymer that includes at least one repeat unit represented by a structure selected from the group consisting of Structural Formulas (I), (II), (III), (IV) and combinations thereof:

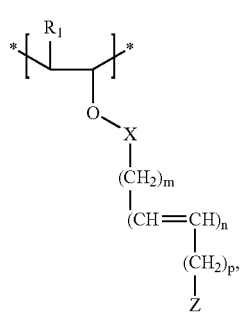

(I)

-continued

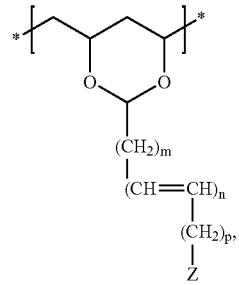

(II)

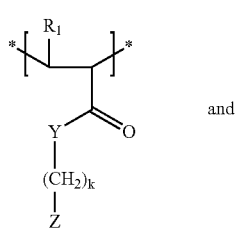

(III)

and (IV)

R' is a covalent bond, —O—, —C(O)O—, —C(O)N—, —C(O)—, —CH=CH—, —S— or —N—.

$R_1$ is —H or an alkyl group, or —(CH$_2$)$_k$—O—X-Z. Typically, $R_1$ is —H or alkyl.

Each X is independently a covalent bond, —C(O)—, —C(O)O— or —C(O)N—.

Y is —O—, —N— or —S—.

Each Z is an independently selected antioxidant.

a is an integer from 0 to 12.

Each k is independently an integer from 0 to 12.

m is an integer from 0 to 6.

n is 0 or 1.

p is an integer from 0 to 6.

An additional aspect of the invention includes a method of enhancing the antioxidant activity of an antioxidant molecule that involves:

i) forming a polymer having reactive pendant groups, wherein the polymer does not include cyclic anhydride repeat units; and ii) derivatizing the polymer with the antioxidant molecule.

One advantage of antioxidant polymers of the present invention is that they can be expected to be less toxic or even non-toxic to animals, by virtue of being largely unabsorbed. Also, these polymers can be generally more potent than small molecule antioxidants, so that a smaller quantity of antioxidant can typically be needed to achieve the same protective effect. In addition, the antioxidant polymers can be blended into another polymeric material or can form a thin film coating on the material, and unlike a small molecule antioxidant, diffusion out of the polymeric material can typically occur slowly.

BRIEF DESCRIPTION OF THE DRAWING

The FIGURE is a high-resolution NMR spectra of (A) poly(vinyl alcohol), (B) 3-(3,5-di-tert-butyl-4-hydroxyphenyl)propionic acid and (C) the antioxidant polymer formed in Example 1.

DETAILED DESCRIPTION OF THE INVENTION

The invention is generally directed to polymers having pendant antioxidant moieties, various compositions containing such polymers, and methods of preparing and using such polymers.

Polymers of the present invention are typically prepared by first preparing or obtaining a polymer having reactive pendant groups. The polymers can be prepared, for example, by chemical or enzymatic methods. Reactive pendant groups can be directly coupled to another moiety having a complementary reactive functional group or can be activated before coupling to another functional group. The polymer having reactive functional groups can be derivatized with an antioxidant. This antioxidant reacts with the reactive pendant group so that the antioxidant becomes attached to the polymer backbone. The antioxidant typically contains a functional group that can be capable of reacting with the pendant functional group of the polymer or can be activated to react with the pendant functional group.

In one embodiment, the polymer does not include cyclic anhydride repeat units.

An antioxidant can be attached to the polymer by one or more linkages or bonds. Examples of suitable linkages include acetal, amide, amine, carbamate, carbonate, ester, ether and thioether linkage. Carbon-carbon bonds can be also suitable. As used herein, an amide is distinguished from a diacyl hydrazide.

There are many examples of polymers that can be derivatized with an antioxidant. One type of such polymer has pendant hydroxyl groups, such as poly(vinyl alcohol) and copolymers thereof (e.g., poly(ethylene-co-vinyl alcohol)). The hydroxyl groups of poly(vinyl alcohol), a polyhydroxyalkyl methacrylate (e.g., polyhydroxy methyl methacrylate), and poly(ethylene-co-vinyl alcohol) react with an antioxidant to form the derivatized antioxidant polymer. Another type of derivatizable polymer contains pendant carboxylic acid groups or esters thereof, such as poly(acrylic acid), poly(alkylacrylic acid) and esters thereof. Poly(acrylic acid) is a preferred polymer; the carboxylic acid groups of poly(acrylic acid) can be derivatized, although carboxylic acid groups generally require activation before derivatization can occur.

An additional type of derivatizable polymer can be a poly(substituted phenol), where the substituted phenol has a substituent with a nucleophilic or electrophilic moiety. Such poly(substituted phenols) can include repeat units represented by the following structural formulas:

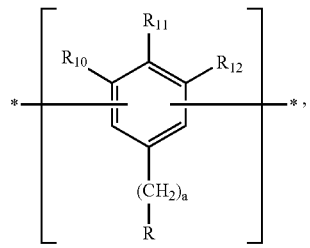

where a is an integer from 0 to 12; R is —OH, —COOH, —NH$_2$, —SH or a halogen; and R$_{10}$, R$_{11}$ and R$_{12}$ are each independently —H, —OH, —NH$_2$ or —SH, provided that at least one of R$_{10}$, R$_{11}$ and R$_{12}$ is —OH, —NH$_2$ or —SH. Preferably, one of R$_{10}$, R$_{11}$ and R$_{12}$ is —OH and the remaining two are optionally —H. More preferably, R$_{11}$ is —OH and R$_{10}$ and R$_{12}$ are —H.

The derivatizable polymers can be homopolymers or copolymers. Copolymers include, for example, block, star, hyperbranched, random, gradient block, and alternate copolymers. The derivatizable polymers can be branched or linear, but are preferably linear.

In copolymers, it is only necessary for one repeat unit to include a pendant reactive group. Second and further repeat units of a copolymer can optionally include a pendant reactive group. For example, about 1% to 100%, such as 10% to 50% or 50% to 100%, of the repeat units of a polymer include pendant functional groups.

All or a fraction of the pendant reactive groups of a derivatizable polymer can be derivatized with an antioxidant. In one example, about 100% of the pendant reactive groups can be derivatized. In another example, about 5% to about 90%, such as about 20% to about 80% (e.g., about 50% to about 80%) of the pendant reactive groups can be derivatized.

These polymers can be minimally derivatized with a single type of antioxidant, but can be derivatized with two or more antioxidants (e.g., chemically distinct antioxidants). When there can be two or more antioxidants, they can be in the same class, as described below, or can be in different classes. The ratio of antioxidants can be varied in order to obtain a polymer having a desired set of properties. For example, when a polymer can be derivatized with two antioxidants, the ratio of a first antioxidant to a second antioxidant can be from about 20:1 to about 1:20, such as from about 5:1 to about 1:5 (e.g., about 1:1).

Many antioxidants can be suitable for use in the present invention, provided that they can be attached to a polymer and retain their antioxidant activity. One class of suitable antioxidants can be phenolic antioxidants. Phenolic antioxidants typically have one or more bulky alkyl groups (alkyl groups having a secondary or tertiary carbon alpha to the phenol ring) ortho or meta, preferably ortho, to the phenol hydroxyl group. Phenolic antioxidants can alternatively have an alkylenedioxy substituent, an alkoxycarbonyl substituent, a 1-propenyl-3-carboxylic acid substituent or an ester thereof. A preferred bulky alkyl group is a tert-butyl group. The phenol hydroxyl group can be protected by a removable protecting group (e.g., an acyl group). Phenolic antioxidants for use in the present invention also generally have a substituent that can react with the pendant reactive group of one of the polymers described above to form a covalent bond between the antioxidant and the polymer.

One group of suitable phenolic antioxidants can be represented by Structural Formula (V):

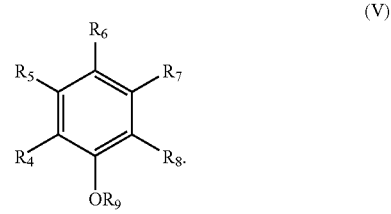

R$_9$ is —H or a substituted or unsubstituted alkyl, acyl or aryl group, preferably —H or an acyl group.

R$_4$, R$_5$, R$_6$, R$_7$ and R$_8$ are independently chosen substituent groups, such that at least one substituent can be a substituted or unsubstituted alkyl or aryl group, a substituted or unsubstituted alkoxycarbonyl group, a substituted or unsubstituted alkylenedioxy group, a 1-propenyl-3-carboxylic acid group or an ester thereof. Also, at least one of R$_4$, R$_5$, R$_6$, R$_7$ and R$_8$ must be a substituent capable of reacting with the pendant reactive group of the polymers described above, such as a substituent having a nucleophilic or electrophilic moiety. Other suitable substituents include, for example, —H, —OH, —NH and —SH. A substituent should not decrease the antioxidant activity more than two-fold; instead, substituents preferably increase the antioxidant activity of the molecule.

Specific examples of phenolic antioxidants that can be attached to a polymer include phenolic antioxidant can be selected from the group consisting of 3-(3,5-di-tert-butyl-4-hydroxyphenyl)propionic acid, 3,5-di-tert-butyl-4-hydroxybenzenethiol, 2-(3,5-di-tert-butyl-4-hydroxyphenyl)acetic acid, 3,5-di-tert-butyl-4-hydroxybenzoic acid, 3,5-di-tert-butyl-4-hydroxycinnamic acid, gallic acid, alkyl gallates, 3,5-di-tert-butyl-4-hydroxybenzyl alcohol, tert-butyl-hydroquinone, 2,5-di-tert-butyl-hydroquinone, 2,6-di-tert-butyl-hydroquinone, 3,5-di-tert-butyl-4-hydroxybenzaldehyde, monoacetoxy-tert-butylhydroquinone, sesamol, isoflavones, flavanoids and coumarins.

Another antioxidant that can be attached to one of the polymers described above can be ascorbic acid or a molecule that contains an ascorbic acid moiety. Typically, ascorbic acid attached to a polymer has the following configuration:

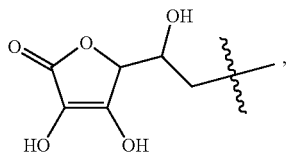

where this moiety can be attached to the polymer by an ether or ester linkage.

Examples of repeat units in polymers of the invention are represented by Structural Formulas (I), (II), (III) and (IV):

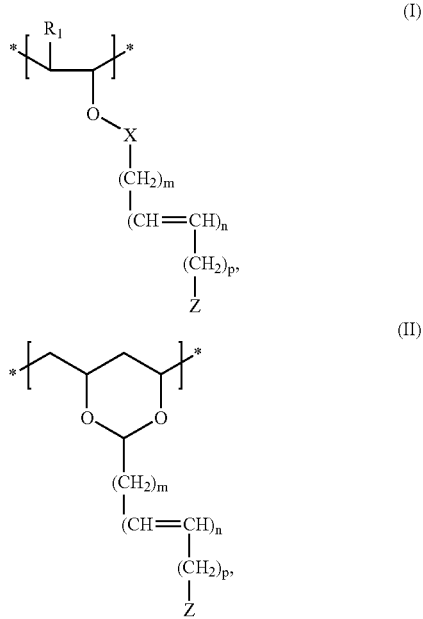

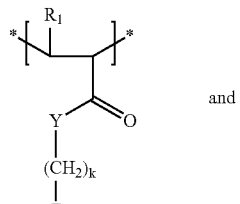

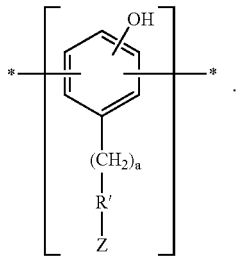

R' is a covalent bond, —O—, —C(O)O—, —C(O)N—, —C(O)—, —CH═CH—, —S— or —N—.

R$_1$ is —H or an alkyl group, or —(CH$_2$)$_k$—O—X-Z. Typically, R$_1$ is —H or alkyl, preferably —H or C$_1$-C$_4$ alkyl group (e.g., methyl).

Each X is independently a covalent bond, —C(O)—, —C(O)O— or —C(O)N—, preferably a covalent bond or —C(O)—.

Y is —O—, —N— or —S—.

Each Z is an independently selected antioxidant.

a is an integer from 0 to 12.

Each k is independently an integer from 0 to 12.

m is an integer from 0 to 6.

n is 0 or 1.

p is an integer from 0 to 6.

Polymers of the invention can include repeat units represented by one or more of Structural Formulas (I)-(IV). Typically, polymers of the invention include repeat units represented by one of Structural Formulas (I)-(IV). Such polymers can be homopolymers or copolymers. One type of copolymer includes ethylene repeat units, particularly in a copolymer containing repeat units represented by Structural Formula (I) and/or Structural Formula (II).

In one embodiment of the invention, a polymer comprises repeat units represented by Structural Formula (I). In a first group of such polymers, the sum of m and p is typically two or greater. When the sum of m and p is greater than two, Z is typically a phenolic antioxidant, as described above. One preferred phenolic antioxidant is a 3,5-di-tert-butyl-4-hydroxyphenyl group, particularly when X is —C(O)—. For these values of X and Z, m is preferably 2 and n and p are each 0. A second preferred antioxidant is a 3,4,5-trihydroxyphenyl group, particularly when X is —C(O)—. Other preferred antioxidants are mono and di-tert-butylated-4-hydroxyphenyl groups, 4-acetoxy-3-tert-butylphenyl groups and 3-alkoxycarbonyl-2,6-dihydroxyphenyl groups (e.g., 3-propoxycarbonyl-2,6-dihydroxyphenyl groups), particularly when X is a covalent bond.

In a second set of these polymer having repeat units represented by Structural Formula (I), m and p are each 0. When m and p are 0, n is also typically 0. For these values of m, n and p, Z is typically ascorbic acid. X is typically a covalent bond. Alternatively, Z is a 3,4,5-trihydroxyphenyl group or a 4-acetoxy-3-tert-butylphenyl group, particularly when X is —C(O)—.

In another embodiment of the invention, an antioxidant polymer has repeat units represented by Structural Formula (II). For these polymers, m, n and p are each typically 0. Z is preferably a phenolic antioxidant, specifically a 3,4,5-trihydroxyphenyl, 3,5-di-tert-butyl-4-hydroxyphenyl group or a 3,5-di-tert-butyl-2-hydroxyphenyl group.

A further embodiment of the invention involves polymers that include repeat units represented by Structural Formula (III). In one group of such polymers, Y is —O— and Z is preferably ascorbic acid, particularly when k is 0. In another group, Y is —O— and Z is a phenolic antioxidant, particularly when k is 0 to 3; more preferably, k is 1. A preferred phenolic antioxidant is a 3,5-di-tert-butyl-4-hydroxyphenyl group. Other examples include of phenolic antioxidants include 4-acetoxy-3-tert-butylphenyl, 3-tert-butyl-4-hydroxyphenyl, 2,6-di-tert-butyl-4-mercaptophenyl and 2,6-di-tert-butyl-4-hydroxyphenyl groups.

In yet another embodiment of the invention, a polymer includes repeat units represented by Structural Formula (IV). Typically, R' is a covalent bond or —OH in such polymers. Other typical values of R' are amide and ester linkages. Preferred Z groups can be phenolic antioxidants, as described above. For these polymers, the phenol hydroxyl group is typically para or meta to the group containing Z, more typically para.

The conditions (e.g., temperature, pressure, atmosphere, concentrations, pH, solvents) for derivitizing a polymer having pendant reactive groups with an antioxidant can depend, in part, upon the nature of the functional groups that can be being reacted. The functional groups to be reacted can be selected such that a covalent bond can be formed between the polymer and the antioxidant. There can be a large number of possible combinations of functional groups that can be present as the pendant reactive group and on the antioxidant that can be suitable for connecting the two components. For example, alcohols and amines can be readily attached to an activated carboxylic acid such as an acid chloride or a carboxylic acid reacted with a carbodiimide (e.g., dicyclohexylcarbodiimide). In addition, alkyl halides (excepting fluorides) can be reacted with a wide variety of nucleophiles (e.g., alcohols, amines, thiols, carbanions) to form a covalent bond. The Mitsunobu reaction can be used to form an ether linkage from two hydroxyl groups. An aldehyde can react with hydroxyl groups to form an acetal linkage. Such coupling reactions are well-known in the art.

The conditions for derivatization can also depend, in part, upon the solubility characteristics of the polymer to be derivatized. Although a polymer may not solubilize, a solvent can be chosen such that the pendant reactive groups can be compatible with the solvent. For example, hydroxyl and carboxylic acid groups can be compatible with a polar solvent.

Methods of inhibiting the oxidation of a substance involve contacting the substance with an antioxidant polymer, as described herein.

For purposes of the present invention, a "method of inhibiting oxidation" is defined as a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

Antioxidant polymers of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1000 amu and less than about 1,000,000 amu, greater than about 1000 amu and less than about 100,000 amu, greater than about 2,000 amu and less than about 10,000 amu, or greater than about 2,000 amu and less than about 5,000 amu. For food or edible products (e.g., products fit for human consumption), the molecular weight can be advantageously selected to be large enough so that an antioxidant polymer cannot be absorbed by the gastrointestinal tract, such as greater than 1000 amu. For antioxidant polymers blended with a polymeric material, the molecular weight can be advantageously selected such that the rate of diffusion of the antioxidant polymer through the polymeric material can be slow relative to the expected lifetime of the polymeric material.

Antioxidant polymers of the present invention can be typically insoluble in aqueous media. The solubility of the antioxidant polymers in non-aqueous media (e.g., oils) depends upon the molecular weight of the polymer, such that high molecular weight polymers can be typically sparingly soluble in non-aqueous media. When an antioxidant polymer of the invention can be insoluble in a particular medium or substrate, it can be preferably well-mixed with that medium or substrate.

Antioxidant polymers of the present invention can be present in a wide variety of compositions where free radical mediated oxidation leads to deterioration of the quality of the composition, including edible products such as oils, foods (e.g., meat products, dairy products, cereals, beverages, crackers, potato flakes, bakery products and mixes, dessert mixes, nuts, candies, etc.), and other products containing fats or other compounds subject to oxidation (e.g., chewing gum, flavorings, yeast, etc.).

Antioxidant polymers additionally can protect edible products such as vitamins, e.g., antioxidant vitamins (Vitamin A, Vitamin C, Vitamin E).

Antioxidant polymers can also be present in plastics and other polymers, elastomers (e.g., natural or synthetic rubber), petroleum products (e.g., mineral oil, fossil fuels such as gasoline, kerosene, diesel oil, heating oil, propane, jet fuel), adhesives, lubricants, paints, pigments or other colored items, cosmetic compositions, e.g., soaps and cosmetics (e.g., creams, lotions, hair products). Soaps and cosmetics, in particular, benefit from the addition of a large proportion of one or more antioxidant polymers of the invention. Soaps and cosmetics can contain, for example, about 1% to about 20% (e.g., about 5% to about 15%) by weight of antioxidant polymer.

The antioxidant polymers can be used to coat a metal as a rust and corrosion inhibitor.

Antioxidant polymers additionally can protect pharmaceutical products (i.e., those containing a pharmaceutically active agent) from degradation. The addition of antioxidant polymers can be particularly advantageous when the vitamin or pharmaceutically active agent can be present in a liquid composition, although the antioxidant polymers can be expected also to have a benefit in solid compositions.

In food products, the antioxidant polymers can prevent rancidity. In plastics, the antioxidant polymers can prevent the plastic from becoming brittle and cracking.

Antioxidant polymers of the present invention can be added to oils to prolong their shelf life and properties. These oils can be formulated as vegetable shortening or margarine. Oils generally come from plant sources and include cottonseed oil, linseed oil, olive oil, palm oil, corn oil, peanut oil, soybean oil, castor oil, coconut oil, safflower oil, sunflower oil, canola (rapeseed) oil and sesame oil. These oils contain one or more unsaturated fatty acids such as caproleic acid, palmitoleic acid, oleic acid, vaccenic acid, elaidic acid, brassidic acid, erucic acid, nervonic acid, linoleic acid, eleosteric acid, alpha-linolenic acid, gamma-linolenic acid, and arachidonic acid, or partially hydrogenated or trans-hydrogenated variants thereof. Antioxidant polymers of the present invention can be also advantageously added to food or other consumable products containing one or more of these fatty acids.

The shelf life of many materials and substances contained within the materials, such as packaging materials, can be enhanced by the presence of an antioxidant polymer of the present invention. The addition of an antioxidant polymer to a packaging material is believed to provide additional protection to the product contained inside the package. In addition, the properties of many packaging materials themselves, particularly polymers, can be enhanced by the presence of an antioxidant regardless of the application (i.e., not limited to use in packaging). Common examples of packaging materials include paper, cardboard and various plastics and polymers. A packaging material can be coated with an antioxidant polymer (e.g., by spraying the antioxidant polymer or by applying as a thin film coating), blended with or mixed with an antioxidant polymer (particularly for polymers), or otherwise have an antioxidant polymer present within it. In one example, a thermoplastic polymer such as polyethylene, polypropylene or polystyrene can be melted in the presence of an antioxidant polymer in order to minimize its degradation during the polymer processing. An antioxidant polymer can also be co-extruded with a polymeric material.

One example of a packaging material included in the present invention can be commonly referred to as "smart packaging". Smart packaging can be designed such that it controls gas exchange through the packaging. Examples of smart packaging are described in U.S. Pat. Nos. 5,911,937, 5,320,889 and 4,977,004, the contents of which are incorporated herein in their entirety. One conventional type of smart packaging involves a layer of an oxygen barrier such as nylon or poly(ethylene-co-vinyl alcohol) that can be typically sandwiched between one or more layers of a moisture-resistant polymer or polymer blend such as poly-ethylene terephthalate, poly(vinylidene chloride), poly(vinyl chloride), poly(ethylene) or poly(propylene). The layers of moisture-resistant polymer can be either the same or different. In the present invention, one or more of the antioxidant polymers described herein can be added as an additional layer or can be blended with a layer of the packaging material. Alternatively, all or a fraction of the hydroxyl groups of poly(ethyelene-co-vinyl alcohol) itself can be derivatized with an antioxidant, such as in a polymer represented by Structural Formula (I) or Structural Formula (II). Such polymers can be expected to serve both as an oxygen barrier and as an antioxidant. It is believed that the advantage of a derivatized poly(ethylene-co-vinyl alcohol) is that the moisture-resistant layers that can be typically used to protect poly(ethylene-co-vinyl alcohol) from adsorbing water molecules (and thereby losing its oxygen resistance) can be eliminated in some embodiments, such that only a single layer of polymer can be required.

Polymers of the present invention can generally be added to another antioxidant or polymer e.g., forming combinations of one or more antioxidant polymers described herein and one or more synthetic and/or natural monomeric and/or oligomeric antioxidants and/or preservatives. Such compositions can be expected to have both short-term and long-term antioxidant activity. The known antioxidants can be typically small molecules (e.g., ascorbic acid, tocopherols, phenolic antioxidants such as BHA, BHT, TBHQ and propyl gallate). The ratio of polymeric antioxidant to small molecule antioxidant can be controlled to give desired properties. For example, the weight ratio of polymeric antioxidant to conventional antioxidant can be from about 1:100 to about 100:1, such as about 1:10 to about 10:1.

The total concentration or amount of a polymer described herein that can be present in a composition depends, in part, upon the antioxidant activity of the polymer and the amount of antioxidant protection required. For example, the concentration of polymer can be as high as 10% by weight of a product (e.g., in cosmetics and packaging materials), but can be typically present at a concentration of about 0.1 ppm to about 10,000 ppm, more typically about 0.1 ppm to about 100 ppm.

An alkyl group is a saturated hydrocarbon in a molecule that is bonded to one other group in the molecule through a single covalent bond from one of its carbon atoms. Examples of lower alkyl groups include methyl, ethyl, n-propyl, iso-propyl, n-butyl, sec-butyl and tert-butyl. An alkoxy group is a substituted or unsubstituted alkyl group where an oxygen atom connects the alkyl group and one other group. An acyl group is a substituted or unsubstituted alkyl group that contains a terminal carbonyl moiety.

Aryl groups include carbocyclic aryl groups such as phenyl, 1-naphthyl, 2-naphthyl, 1-anthracyl and 2-anthracyl, and heterocyclic aryl groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aryl groups also include fused polycyclic aromatic ring systems in which a carbocyclic aromatic ring or heteroaryl ring can be fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Examples of suitable substituents on an alkyl, aryl or acyl group may include, for example, halogen (—Br, —Cl, —I and —F), —OR$_a$, —CN, —NO$_2$, —N(R$_a$)$_2$, —COOR$_a$, —CON(R$_a$)$_2$, —SO$_k$R$_a$ (k' is 0, 1 or 2) and —NH—C (=NH)—NH$_2$. An alkyl group can also have =O or =S as a substituent. Each R$_a$ is independently —H, an alkyl group, a substituted alkyl group, a benzyl group, a substituted benzyl group, an aryl group or a substituted aryl group. A substituted benzylic group or aryl group can also have an alkyl or substituted alkyl group as a substituent. A substituted alkyl group can also have a benzyl, substituted benzyl, aryl or substituted aryl group as a substituent. A substituted alkyl, substituted aryl or substituted acyl group can have more than one substituent.

The following examples are not intended to be limiting in any way.

EXAMPLE 1

3-(3,5-di-tert-butyl-4-hydroxyphenyl)propionic acid was dissolved in dry dichloromethane (DCM) and oxalyl chloride was added to the solution and was stirred for 1 hour, thereby forming an acid chloride.

In a separate flask, poly(vinyl alcohol) (PVA) was dissolved in dry dimethylformamide (DMF) by heating at 60° C. for 15 minutes. Small amounts of triethylamine and dimethylaminopyridine (DMAP) were added to this solution. The resulting solution was kept in an ice bath and to it was added the solution of the acid chloride over a period of one hour. The reaction was performed under an inert nitrogen atmosphere. After the reaction appeared to be complete, the solution was stirred in the ice bath for an additional 5 hours. The mixture was stirred for another one or two days at room temperature. The solvents were then removed by rotary evaporation to obtain a solid residue. The solid residue was washed first with a 10% sodium bicarbonate solution, followed by a 0.1 M HCl solution. The residue was then treated with a brine (NaCl) solution. Finally, the residue was washed with a 25% methanol-water mixture. The residue was dried under vacuum for 24 hours. The product residue was analyzed by $^1$H and $^{13}$C NMR spectrometry (The FIGURE).

Spectrum C in the FIGURE shows the absence of a resonance peak (d) due to the —COOH groups present in 3-(3,5-di-tert-butyl-4-hydroxyphenyl)propionic acid and shows the presence of resonance peaks due to the aromatic and aliphatic protons of the this antioxidant moiety. Resonance peaks due to the methylene and methine groups in PVA are also present in Spectrum C. This suggests that the antioxidant moiety has been attached to PVA. However, the presence of the resonance peaks for the —OH groups of PVA suggest that not all —OH groups have been derivatized with the antioxidant. The integral ratio of methine proton (b) and the hydroxyl proton (c) in PVA (Spectrum A) is 1:1, as expected, but can be changed to 1 (b'):0.8 (c') in the product polymer (Spectrum C). This suggests that 20% of the hydroxyl groups are derivatized by the method described above.

The antioxidant activity of 3-(3,5-di-tert-butyl-4-hydroxyphenyl)propionic acid and the derivatized polymer prepared above were measured according to the procedure published in *Food Chemistry* 73:285-290 (2001). The results are presented in Table 1.

TABLE 1

Comparison of Antioxidant Activities of 3-(3,5-di-tert-butyl-4-hydroxyphenyl) propionic acid and the Derivatized Polymer

| Concentration | Compound | Antioxidant Activity | Enhancement Factor |
|---|---|---|---|
| 20 ppm | 3-(3,5-di-tert-butyl-4-hydroxyphenyl) propionic acid | 24.8% | |
| 100 ppm | Derivatized Polymer | 36.2% | 32% |

The degree of substitution of the antioxidant moiety on PVA is 20%, which means that 100 ppm of the derivatized polymer contains only 20 ppm of 3-(3,5-di-tert-butyl-4-hydroxyphenyl)propionic acid. The antioxidant activity of 20 ppm of 3-(3,5-di-tert-butyl-4-hydroxyphenyl)propionic acid was 24.8% and the antioxidant activity of 100 ppm of the derivatized polymer was 36.2%. Thus, the antioxidant attached to the polymer has 32% greater activity than the antioxidant by itself. It can be expected that a polymer having 100% derivatization would have a further increase in antioxidant activity.

EXAMPLE 2

Poly(acrylic acid) is reacted with ascorbic acid in the presence of p-toluene sulfonic acid (PTSA) and dicyclohexylcarbodiimide (DCC), thereby attaching the antioxidant to the polymer by an ester linkage.

EXAMPLE 3

Poly(acrylic acid) is reacted with 3,5-di-tert-butyl-4-hydroxybenzyl alcohol in the presence of DCC and PTSA, thereby attaching the antioxidant to the polymer by an ester linkage.

EXAMPLE 4

Poly(vinyl alcohol) is reacted with 1-tert-butyl-4-hydroxyphenol in the presence of diethyl azodicarboxylate, triphenyl phosphine and DMF (e.g., the Mitsunobu reaction), thereby attaching the antioxidant to the polymer by an ether linkage.

EXAMPLE 5

2,5-di-tert-butylhydroquinone or propyl gallate is attached to poly(vinyl alcohol) by the procedure of Example 4.

EXAMPLE 6

1-tert-butyl-4-hydroxyphenol, 2,5-di-tert-butylhydroquinone or propyl gallate is coupled to poly(ethylene-co-vinyl alcohol) by the procedure of Example 4.

EXAMPLE 7

Poly(vinyl alcohol) is reacted with 3,5-di-tert-butyl-4-hydroxybenzaldehyde, 3,4,5-trihydroxybenzaldehyde or 3,5-di-tert-butyl-2-hydroxybenzaldehyde in the presence of PTSA and DCC, thereby attaching the antioxidant to the polymer by an acetal linkage.

EXAMPLE 8

Poly(acrylic acid) is reacted with 3,5-di-tert-butyl-4-hydroxybenzyl alcohol and ascorbic acid to form ester linkages, such as by the procedures of Examples 2 and/or 3.

EXAMPLE 9

Poly(vinyl alcohol) is reacted with 2,5-di-tert-butylhydroquinone, propyl gallate and tert-butylhydroquinone by the Mitsunobu reaction.

While this invention has been particularly shown and described with references to preferred embodiments thereof, it will be understood by those skilled in the art that various changes in form and details may be made therein without departing from the scope of the invention encompassed by the appended claims.

What is claimed is:

1. An antioxidant polymer, comprising at least one repeat unit that is represented by a structure selected from the group consisting of Structural Formulas (I), (II), (III), (IV) and combinations thereof:

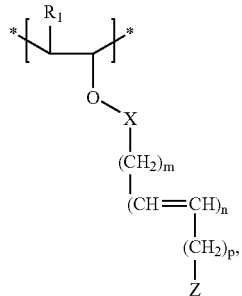

(I)

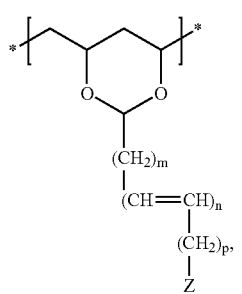

(II)

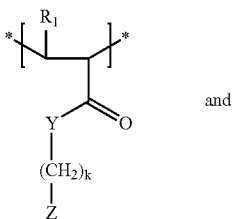 and (III)

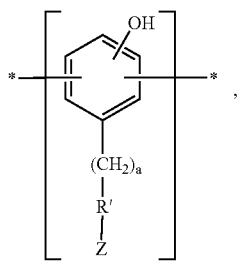

(IV)

wherein:
R' is a covalent bond, —O—, —C(O)O—, —C(O)N—, —C(O)—, —CH═CH—, —S— or —N—;
R$_1$ is —H or an alkyl group, or —(CH$_2$)$_k$—O—X—Z;
each X is independently a covalent bond, —C(O)—, —C(O)O— or —C(O)N—;
Y is —O—, —N— or —S—;
each Z is an independently selected antioxidant;
a is an integer from 0 to 12;
each k is independently an integer from 0 to 12;
m is an integer from 0 to 6;
n is 0 or 1; and
p is an integer from 0 to 6, and wherein when the repeat unit is represented by Structural Formula (I), (II) or (III), Z is selected from the group consisting of

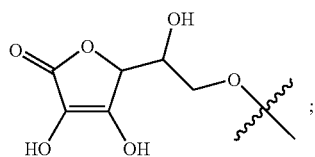

a 4-acetoxy-3-tert-butylphenyl group, a 3-alkoxycarbonyl-2,6-dihydroxyphenyl group, a 3-propoxycarbonyl-2,6-dihydroxyphenyl group, a 3,5-di-tert-butyl-2-hydroxyphenyl group, a 3-tert-butyl-4-hydroxyphenyl group, a 2,6-di-tert-butyl-4-mercaptophenyl group, a 2,6-di-tert-butyl-4-hydroxyphenyl group, a 3,4-methylenedioxyphenyl group, a 3,5-di-tert-butyl-4-hydroxybenzenethiol, 2-(3,5-di-tert-butyl-4-hydroxyphenyl) acetic acid, 3,5-di-tert-butyl-4-hydroxybenzoic acid, 3,5-di-tert-butyl-4-hydroxycinnamic acid, alkyl gallates, 3,5-di-tert-butyl-4-hydroxybenzyl alcohol, tert-butyl-hydroquinone, 2,5-di-tert-butyl-hydroquinone, 2,6-di-tert-butyl-hydroquinone, 3,5-di-tert-butyl-4-hydroxybenzaldehyde, monoacetoxy-tert-butylhydroquinone, sesamol, isoflavones, flavanoids and coumarins.

2. The antioxidant polymer of claim 1, wherein X is a covalent bond or —C(O)—.

3. The antioxidant polymer of claim 1, wherein the polymer is a homopolymer.

4. The antioxidant polymer of claim 1, wherein the antioxidant polymer is a copolymer.

5. The copolymer of claim 4, wherein the copolymer includes two or more different antioxidants.

6. A composition comprising:
an antioxidant polymer and one or more components selected from the group consisting of: an edible product, a packaging material, a soap, a cosmetic agent, a petroleum product, a lubricant, a paint, an elastomer, a pharmaceutically active agent, a synthetic monomeric or oligomeric antioxidant, a natural monomeric or oligomeric antioxidant, and a preservative, wherein the antioxidant polymer includes at least one repeat unit represented by a structure selected from the group consisting of Structural Formulas (I), (II), (III), (IV) and combinations thereof:

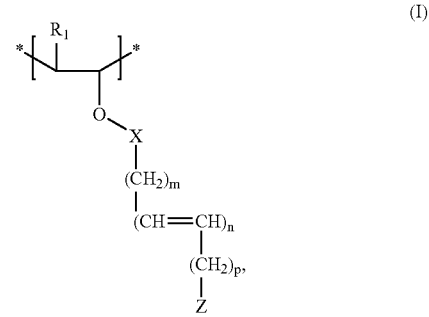

(I)

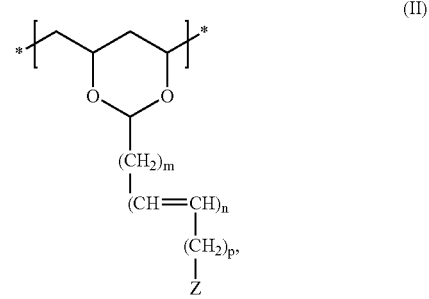

(II)

-continued

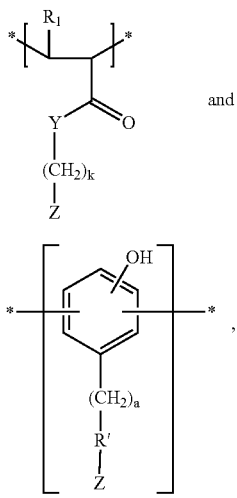

(III)

and (IV)

wherein:
R' is a covalent bond, —O—, —C(O)O—, —C(O)N—, —C(O)—, —CH=CH—, —S— or —N—;
$R_1$ is —H or an alkyl group, or —$(CH_2)_k$—O—X—Z;
each X is independently a covalent bond, —C(O)—, —C(O)O— or —C(O)N—;
Y is —O—, —N— or —S—;
each Z is an independently selected antioxidant;
a is an integer from 0 to 12;
each k is independently an integer from 0 to 12;
m is an integer from 0 to 6;
n is 0 or 1; and
p is an integer from 0 to 6, and wherein when the repeat unit is represented by Structural Formula (I), (II) or (III), Z is selected from the group consisting of

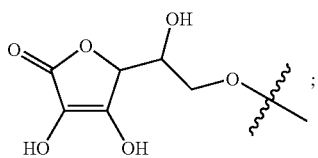

a 3,4,5-trihydroxyphenyl group, 4-acetoxy-3-tert-butylphenyl group, a 3-alkoxycarbonyl-2,6-dihydroxyphenyl group, a 3-propoxycarbonyl-2,6-dihydroxyphenyl group, a 3,5-di-tert-butyl-2-hydroxyphenyl group, a 3-tert-butyl-4-hydroxyphenyl group, a 2,6-di-tert-butyl-4-mercaptophenyl group, a 2,6-di-tert-butyl-4-hydroxyphenyl group, a 3,4-methylenedioxyphenyl group, a 3,5-di-tert-butyl-4-hydroxybenzenethiol, 2-(3,5-di-tert-butyl-4-hydroxyphenyl) acetic acid, 3,5-di-tert-butyl-4-hydroxybenzoic acid, 3,5-di-tert-butyl-4-hydroxycinnamic acid, gallic acid, alkyl gallates, 3,5-di-tert-butyl-4-hydroxybenzyl alcohol, tert-butyl-hydroquinone, 2,5-di-tert-butyl-hydroquinone, 2,6-di-tert-butyl-hydroquinone, 3,5-di-tert-butyl-4-hydroxybenzaldehyde, monoacetoxy-tert-butylhydroquinone, sesamol, isoflavones, flavanoids and coumarins.

* * * * *